United States Patent
Kim et al.

(10) Patent No.: US 10,632,077 B2
(45) Date of Patent: Apr. 28, 2020

(54) PREGABALIN-CONTAINING, ORAL SUSTAINED-RELEASE TRIPLE LAYER TABLET

(71) Applicant: GL PHARMTECH CORP., Gyeonggi-do (KR)

(72) Inventors: Kyung Hun Kim, Gyeonggi-do (KR); Kyung Soo Lee, Gyeonggi-do (KR); Woo Heon Song, Gyeonggi-do (KR); Jun Sang Park, Gyeonggi-do (KR)

(73) Assignee: GL PHARMTECH CORP., Gyeonggi-do (KR)

( * ) Notice: Subject to any disclaimer, the term of this patent is extended or adjusted under 35 U.S.C. 154(b) by 0 days.

(21) Appl. No.: 15/554,379

(22) PCT Filed: Mar. 29, 2017

(86) PCT No.: PCT/KR2017/003377
§ 371 (c)(1),
(2) Date: Aug. 29, 2017

(87) PCT Pub. No.: WO2018/143511
PCT Pub. Date: Sep. 8, 2018

(65) Prior Publication Data
US 2019/0099376 A1  Apr. 4, 2019

(30) Foreign Application Priority Data
Feb. 1, 2017  (KR) .................. 10-2017-0014586

(51) Int. Cl.
| | | |
|---|---|---|
| *A61K 9/20* | (2006.01) | |
| *A61K 47/10* | (2017.01) | |
| *A61K 47/38* | (2006.01) | |
| *A61K 47/32* | (2006.01) | |
| *A61K 47/26* | (2006.01) | |
| *A61K 31/197* | (2006.01) | |
| *A61P 25/08* | (2006.01) | |
| *A61K 9/00* | (2006.01) | |
| *A61K 9/24* | (2006.01) | |

(52) U.S. Cl.
CPC ............ *A61K 9/2086* (2013.01); *A61K 9/205* (2013.01); *A61K 9/2095* (2013.01); *A61K 31/197* (2013.01); *A61K 47/10* (2013.01); *A61K 47/26* (2013.01); *A61K 47/32* (2013.01); *A61K 47/38* (2013.01); *A61P 25/08* (2018.01)

(58) Field of Classification Search
None
See application file for complete search history.

(56) References Cited

U.S. PATENT DOCUMENTS

| | | | |
|---|---|---|---|
| 5,563,175 A | 10/1996 | Silveman et al. | |
| RE41,920 E | 11/2010 | Singh | |
| 2005/0053653 A1* | 3/2005 | Kidane | A61K 9/0004 424/463 |
| 2010/0040681 A1* | 2/2010 | Park | A61K 9/2086 424/472 |
| 2013/0078290 A1* | 3/2013 | Pilgaonkar | A61K 9/0065 424/400 |
| 2014/0161880 A1 | 6/2014 | Woo et al. | |

FOREIGN PATENT DOCUMENTS

| | | | | |
|---|---|---|---|---|
| WO | WO 2014/013006 A1 * | 1/2014 | ............... | A61K 9/20 |
| WO | WO-2014013006 A1 * | 1/2014 | ........... | A61K 9/0065 |

* cited by examiner

*Primary Examiner* — Jeffrey T. Palenik
(74) *Attorney, Agent, or Firm* — SIMI Law Group, P.C.

(57) ABSTRACT

Disclosed a pregabalin-containing, high swellable, oral sustained-release triple layer tablet suitable for administration once daily.

12 Claims, 3 Drawing Sheets

PREGABALIN-CONTAINING, ORAL SUSTAINED-RELEASE TRIPLE LAYER TABLET

CROSS-REFERENCE TO RELATED APPLICATIONS

This application is a national phase application of PCT Application No. PCT/KR2017/003377, filed on Mar. 29, 2017, which claims benefit of Korean Patent Application 10-2017-0014586, filed on Feb. 1, 2017. The entire disclosure of the applications identified in this paragraph are incorporated herein by references.

TECHNICAL FIELD

The present invention relates to a sustained-release triple layer tablet containing pregabalin. More specifically, the present invention relates to a triple layer tablet consisting of an upper layer and a lower layer comprising pregabalin or a pharmaceutically acceptable salt thereof and a swellable polymer; and an intermediate layer comprising pregabalin or a pharmaceutically acceptable salt thereof and a medium transfer agent. The triple layer tablet of the present invention consists of an upper layer and a lower layer comprising a swellable polymer, and an intermediate layer positioned therebetween.

According to the present invention, an aqueous medium (for example, water, gastric fluid, intestinal fluid, etc.) is effectively delivered to the swellable polymer of the upper layer and the lower layer through the medium transfer agent of the intermediate layer, thereby further increasing the swellability. The preparation according to the present invention enables a drug to remain in the gastrointestinal tract for more long time. Thereby, the preparation can improve the absorption efficiency of the drug in the upper portion of the gastrointestinal tract, and control the drug to be released continuously. As such, the preparation according to the present invention is a gastro-retentive sustained-release preparation, and thus this preparation is suitable for administration once daily.

BACKGROUND

Pregabalin is an analog of γ-aminobutyric acid (Gamma-aminobutyric acid, GABA). Its chemical name is (S)-3-(aminomethyl)-5-methylhexanoic acid, its molecular equation is $C_8H_{17}NO_2$, and its molecular weight is 159.23.

U.S. Pat. No. 5,563,175 discloses that γ-aminobutyric acid is useful as antiseizure therapy for central nervous system disorders such as epilepsy, Huntington's chorea, cerebral ischemia, Parkinson's disease, tardive dyskinesia, and the like, and U.S. Pat. No. RE 41,920 discloses that isobutylgaba, glutamic acid and γ-aminobutyric acid, which are derivatives of isobutylgaba, are effective in pain therapy against hyperalgesic and allodynic actions.

Pregabalin is a white or pale yellow crystalline powder, which has a water-soluble property. Pregabalin is bonded to an alpha-2-delta (α2δ) subunit of a calcium channel in the central nerve, and is involved in the regulation of neurotransmitter (γ-aminobutyric acid) activity, and this is used for the treatment of peripheral and central neuropathic pain, epilepsy, fibromyalgia, etc. When pregabalin is orally administered with between 1 and 600 mg, the absorption amount is dose-dependent, the maximum blood level arrival time (Tmax) is between 0.8 to 1.2 hours, and the half-life of a drug is between 5.2 to 6.6 hours. At present, pregabalin has been commercially available in oral capsule products (product name: Lyrica Capsule, Pfizer) that can be administered twice daily at a daily dose of from 150 mg up to 600 mg at maximum, and this can be used only as immediate release formulations.

However, drugs that are administered twice daily or three times daily are inconvenience for patients who take the drugs. Compliance to elderly patients or patients who take drugs for a long time is greatly reduced.

Since pregabalin can be used only in formulations that can be administered twice daily, this is inconvenient in terms of compliance.

If the drug administration method is changed to be administered once daily through the preparation development, there are following advantages that: compliance to patients will be greatly improved; drug concentration in blood can be maintained constantly, thereby reducing or preventing undesired dose-dependent side effects; and drug efficacy can be maintained continuously.

Especially, it has been known that for first administration, pregabalin can be administered twice daily and its dose can be gradually increased from 75 mg for one time up to 600 mg for day at maximum at an interval of 7 days, and the arrival time to a drug steady-state takes 24 to 48 hours after first intake.

Herein, if the dose is gradually increased while observing a drug reaction shown when taking a drug with accurately complying with the dose having high compliance through the method such as an administration once daily, more accurate final dose can be determined in terms of safety and efficiency. This is because, if compliance is low, the dose is not accurate, and thus the final dose which is determined by increasing the dose while observing the drug reaction may be inaccurate.

According to existing clinical studies, it has been known that pregabalin is not absorbed homogeneously in the gastrointestinal tract, and that most of drugs are absorbed by an L-amino acid transporter in the upper portion of the gastrointestinal tract. Therefore, the absorption occurs mainly in the small intestine and the ascending colon, and if the drugs pass through the hepatic flexure, the drugs are hardly absorbed.

It has been known that conventional sustained-release tablets pass through the hepatic flexure at about 6 hours after the administration. Thus, in the case of developing sustained-release tablets containing pregabalin, the tablets will pass through the hepatic flexure at about 6 hours after the administration. However, since pregabalin is hardly absorbed in the hepatic flexure, the drug release of the general pregabalin-containing sustained-release tablets after 6 hours is not clinically significant. As such, since there is a limitation of time when pregabalin is absorbed in the body after the administration, there is a problem in developing formulations that can be administered once daily.

DETAILED DESCRIPTION

Summary of Invention

There is a problem that pregabalin cannot have pharmacokinetic properties suitable for administration once daily, because there is a limitation of site where the drug is absorbed in the gastrointestinal tract and, thus, there is a limitation of absorption time after the administration.

Generally, in order to develop formulations suitable for administration once daily, the drug concentration effective in the body should be maintained for 24 hours. Thus, the drug absorption time of pregabalin should be increased by extending the time until pregabalin passes through the hepatic flexure which is the site where the absorption of pregabalin is limited.

The present invention aims to prepare a pregabalin-containing, high swellable, oral sustained-release triple layer tablet, using a gastroretentive drug delivery system, in order to solve the problems.

Accordingly, the present invention aims to provide a pregabalin-containing sustained-release preparation for oral administration once daily, having pharmacokinetic properties of reducing side effect while increasing compliance and extending the efficacy time duration, as compared to conventional pregabalin-containing preparations for oral administration twice daily.

Technical Solution

The present invention relates to a sustained-release triple layer tablet containing pregabalin. More specifically, the present invention relates to a pregabalin-containing, sustained-release triple layer tablet, comprising an upper layer and a lower layer comprising a swellable polymer; and an intermediate layer comprising a medium transfer agent.

In addition, the present invention relates to a triple layer tablet consisting of an upper layer and a lower layer comprising pregabalin or a pharmaceutically acceptable salt thereof and a swellable polymer; and an intermediate layer comprising pregabalin or a pharmaceutically acceptable salt thereof and a medium transfer agent.

The triple layer tablet of the present invention consists of an upper layer and a lower layer comprising a swellable polymer, and an intermediate layer positioned therebetween.

According to the present invention, the aqueous medium is effectively delivered to the swellable polymer of the upper layer and the lower layer through the medium transfer agent of the intermediate layer, thereby further increasing the swellability. The preparation according to the present invention enables a drug to remain in the gastrointestinal tract for more long time. Thereby, the preparation can improve the absorption efficiency of the drug in the upper gastrointestinal tract, and control the drug to be released continuously. As such, the preparation according to the present invention is a gastro-retentive sustained-release preparation, and thus the preparation is suitable for administration once daily.

Effect of Invention

As for drugs such as pregabalin that are mainly absorbed in the upper portion of the gastrointestinal tract, a preparation suitable for administration once daily was developed by applying the sustained-release preparation technology of adjusting the drug release rate, and the gastro-retentive drug delivery system at the same time.

In the present invention, the swellable polymer is separated into the upper layer and the lower layer, and the medium transfer agent is positioned between the upper layer and the lower layer, so that the large amount of aqueous medium can be rapidly delivered to the swellable polymer. Thus, in the triple layer tablet of the present invention, improved swellability can be obtained as compared to tablets in single matrix forms, and the size change of the tablet is larger than that in tablets in single matrix forms.

As such, tablets with increased size cannot pass through the pylorus and remain in the stomach for a longer period.

Therefore, according to the present invention, the extension of the gastric residence time and the improvement of drug absorption resulting therefrom are possible, thereby providing a sustained-release triple layer tablet that can be administered once daily.

BEST MODE FOR EMBODIMENT OF INVENTION

Figure 1:
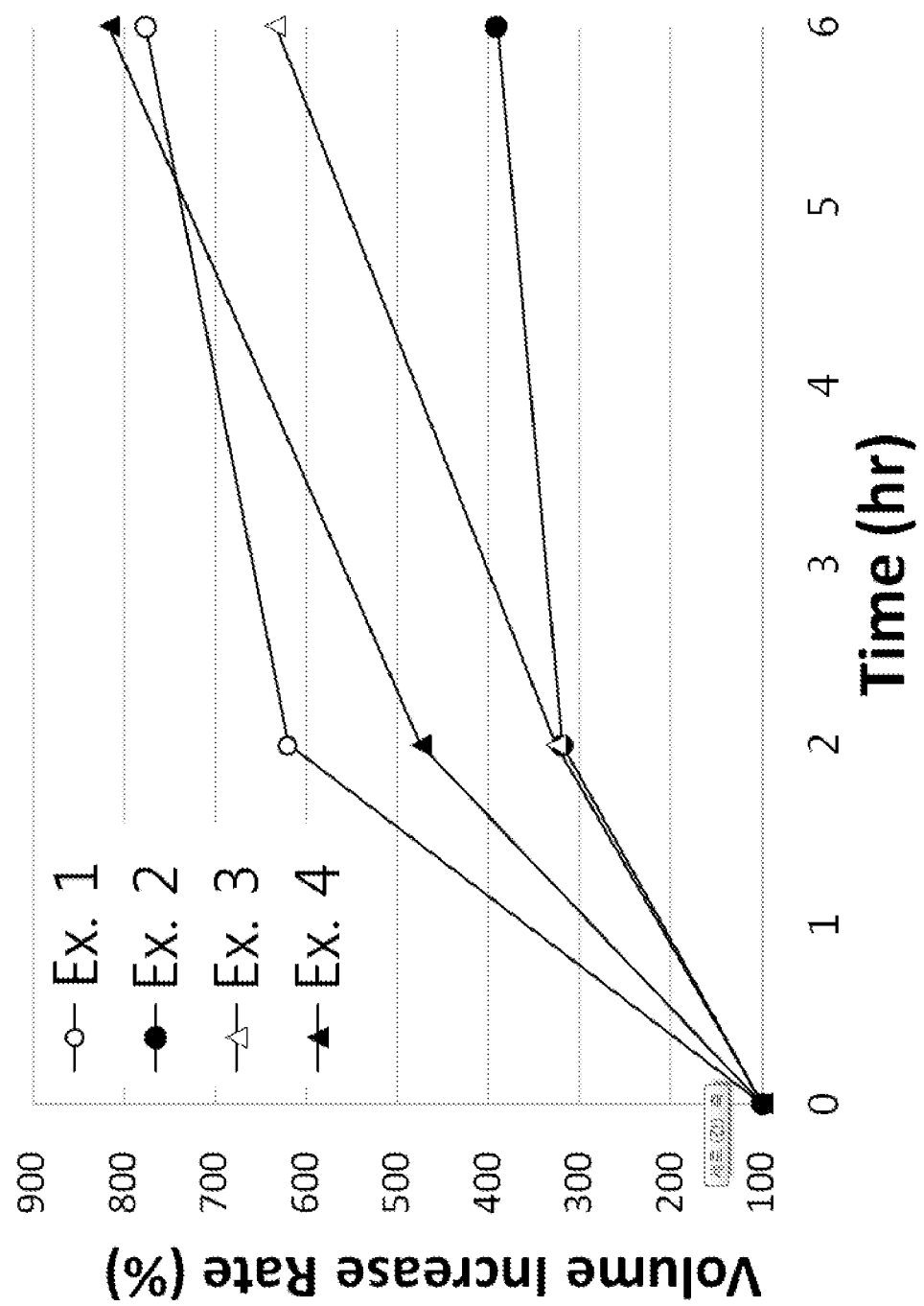
FIG. 1 is a graph comparing the volume changes in the swelling test of the pregabalin-containing oral sustained-release triple layer tablets prepared in Examples 1 to 4.

The present invention relates to a sustained-release triple layer tablet containing pregabalin. More specifically, the present invention relates to a triple layer tablet consisting of an upper layer and a lower layer comprising pregabalin or a pharmaceutically acceptable salt thereof and a swellable polymer; and an intermediate layer comprising pregabalin or a pharmaceutically acceptable salt thereof and a medium transfer agent. The triple layer tablet of the present invention consists of an upper layer and a lower layer comprising a swellable polymer, and an intermediate layer positioned therebetween.

According to the present invention, the aqueous medium is effectively delivered to the swellable polymer of the upper layer and the lower layer through the medium transfer agent of the intermediate layer, thereby further increasing swellability. The preparation according to the present invention enables a drug to remain in the gastrointestinal tract for more long time. Thereby, the preparation can improve the absorption efficiency of the drug in the upper gastrointestinal tract, and control the drug to be released continuously. As such, the preparation according to the present invention is a gastro-retentive sustained-release preparation, so this preparation is suitable for administration once daily.

The oral sustained-release triple layer tablet according to the present invention may have a therapeutically effective amount of pregabalin per unit dosage form.

The triple layer tablet of the present invention consists of three layers, and specifically, consists of an upper layer and a lower layer comprising a swellable polymer, and an intermediate layer comprising a medium transfer agent therebetween. However, depending on cases, the tablet can be prepared as a multilayer tablets consisting of three or more layers comprising said three layers.

When the triple layer tablet of the present invention is in contact with the aqueous medium, the medium transfer agent present in the intermediate layer introduces the aqueous medium into the tablet, and then delivers the aqueous medium to the swellable polymer present in the upper layer and the lower layer, thereby improving the swellability of the upper layer and the lower layer. Such preparation enables a drug to remain in the gastrointestinal tract for more long time, thereby improving the absorption efficiency of the drug in the upper portion of the gastrointestinal tract and controlling the drug to be released continuously, so as to provide an oral sustained-release preparation suitable for administration once daily.

The tablet rapidly swelled by the intermediate layer comprising the medium transfer agent preferably has the size of 12 mm or more, which is the average diameter of the adult pylorus, in order to prevent the tablet from being rapidly released in the stomach. Herein, depending on the shape that can influence when the tablet passes through the pylorus, in the case of round tablets, the size of the tablet refers to a diameter, and in the case of oval or oblong tablets, the size of the tablet refers to a diameter of the minor axis of the tablet.

Although the gastric emptying time of drugs may vary depending on various conditions such as intake of food, etc., it has been known that orally administered formulations generally pass through the stomach in two hours in the fasted state. Thus, the administered formulation should be swelled to be big within two hours, which is difficult to pass through the pylorus and to this end, the volume increase rate within two hours should be at least 250% (that is, swelling to a volume of 2.5 times larger than its original tablet volume), preferably, at least 300% (that is, swelling to a volume of 3 times larger than its original tablet volume). In addition, in order to implement the drug release speed suitable for administration once daily, the volume increase rate up to 6 hours should be at least 250% (that is, swelling to a volume of 2.5 times larger than its original tablet volume), preferably, at least 300% (that is, swelling to a volume of 3 times larger than its original tablet volume), and the volume increase rate up to 6 hours should be preferably equal to or more than the volume increase rate within 2 hours, and should not be reduced than the volume increase rate within 2 hours.

In addition, in the multilayer tablet of the present invention, the length of the minor axis of the tablet at two hours after the tablet is in contact with the aqueous medium is 12 mm or more, and preferably, the length of the minor axis of the tablet for 2 hours to 6 hours after the tablet is in contact with the aqueous medium is at least 12 mm.

In the tablet of the present invention, the upper layer and the lower layer comprise a swellable polymer. Pregabalin, which is an active ingredient, may be comprised in any one of the upper layer and the lower layer or in both of them. The composition or amount of the upper layer and the lower layer may be identical to or different from each other.

The triple layer tablet of the present invention may have various physical forms such as round, oval, oblong, triangle, etc. In consideration of convenience of intake, the smaller size of the prepared tablet is better; however, since the tablet should be rapidly swelled to a size that does not pass through the pylorus after administration of the tablet, after two hours from the swelling test, the diameter of round tablets (or in the case of tablets in different forms, the diameter of the shortest minor axis among the cross sections of the tablets) is preferably 12 mm or more.

The triple layer tablet of the present invention comprises a swellable polymer in the upper layer and the lower layer and a medium transfer agent in the intermediate layer, and pregabalin, which is an active ingredient, may be comprised in all of the upper layer, the intermediate layer and the lower layer, or comprised only in the intermediate layer or in only the upper layer and the lower layer, or in any one of the upper layer and the lower layer depending on cases, in order to exhibit a release speed or a release pattern suitable for administration once daily.

When the triple layer tablet is in contact with the aqueous medium, the medium is penetrated into all of the upper layer, the intermediate layer and the lower layer. The aqueous medium is rapidly penetrated into the center of the tablet through particularly, the medium transfer agent comprised in the intermediate layer, and the aqueous medium penetrated into the intermediate layer of the tablet is rapidly delivered to the upper layer and the lower layer, so that the tablet swells fast to the targeted size. The upper layer and the lower layer rapidly swelled as such swell also to the side of the intermediate layer so that they can be attached to each other. Thus, the size of the tablet swells not only to the up and down longitudinal direction but also to the transverse direction when viewed from the side direction. Through such process, the release speed of pregabalin can be adjusted to be suitable for administration once daily.

In the triple layer tablet of the present invention, the intermediate layer comprises pregabalin and a medium transfer agent. The intermediate layer does not contain a polymer substance, except for a binder used during the granulation preparation process, for rapid delivery of water-solution medium. Thus, the intermediate layer in the triple layer tablet of the present invention is appropriately disintegrated within 30 minutes which are the reference time for general release preparations, in the case of conducting a test only for the intermediate layer, except for the upper layer and the lower layer, according to the disintegration test method among the Korean Pharmacopoeia Disintegration Test Methods.

The medium transfer agent serves, as implied from its name, as providing a route through which water can be rapidly absorbed into the preparation and delivering the absorbed water to the swellable polymer of the upper layer and the lower layer when the triple layer tablet is in contact with gastric fluid after intake or in contact with the aqueous medium during the dissolution test, thereby increasing the swelling speed of the tablet to increase the size of the triple layer tablet.

It was confirmed that the triple layer tablet of the present invention swelled in such manner has greatly increased swelling speed and swelling maintenance time as compared to general single layer tablets comprising a swellable polymer and a medium transfer agent together.

In the present invention, the amount of the medium transfer agent comprised in the intermediate layer of the triple layer tablet is preferably 10% (w/w) to 70% (w/w), more preferably, 10% (w/w) to 50% (w/w), relative to the total amount of the swellable polymer comprised in the upper layer and the lower layer.

As the medium transfer agent of the present invention, substances with good solubility to water or substances which have wicking of inducing penetration of medium even if its solubility is low are used as pharmaceutically acceptable excipients having high affinity with the aqueous medium.

As excipients having good solubility, excipients having solubility defined as "freely soluble" in the Korean Pharmacopoeia Solubility Standard Table (for example, not less than 1 mL and not more than 10 mL of solvent is required to dissolve solute 1 g) are suitable. As such excipients, sugars (for example, dextrose, dextrate, dextrin, lactose, sucrose, glucose, mannitol, isomalt, xylitol, erythritol and sorbitol, etc.), polyvinylpyrrolidone, salts (for example, sodium chloride, magnesium chloride, sodium phosphate, etc.), organic acids (for example, fumaric acids, tartaric acid, etc.) or a mixture thereof can be used Substances which have wicking of inducing penetration of an aqueous medium have the hydrophilic property even though its solubility to water is low and have roles as absorbing the aqueous medium and inducing such that the aqueous medium can be penetrated continuously. As excipients corresponding thereto, starch (for example, corn starch, potato starch, pre-gelatinized starch, etc.), microcrystalline cellulose, low-substituted hydroxypropylcellulose or a mixture thereof can be used.

The upper layer, the lower layer and the intermediate layer in the triple layer tablet of the present invention each may optionally comprise a pharmaceutically acceptable binder. The binder is contained in the amount of less than 20% (w/w) relative to the weight of each layer in which the binder is comprised. The binder can be used for preparing a granule containing a pharmaceutical active material and a swellable polymer, as needed. As the binders, polyvinylpyrrolidone, copovidone, low-viscosity hypromellose having a viscosity of 100 cps or less in an aqueous solution 2% (w/w) (at 20° C.) or a mixture thereof can be used.

The triple layer tablet of the present invention may optionally comprise one or more lubricants that are required for the preparation process steps including smooth mixing or tableting process in each layer. The lubricants are comprised in the amount of less than 3% (w/w), preferably, in the range of 1% (w/w) to 3% (w/w), relative to the weight of each layer in which the lubricants are comprised. As the lubricants, talc, stearate or metal salt thereof (for example, calcium stearate, magnesium stearate, etc.), stearic esters (for example, polyoxyethylene stearate, glyceryl monostearate, glyceryl palmitostearate, etc.), glyceryl behenate, polyethylene glycol, benzoic acids or a mixture thereof can be used.

The swellable polymer comprised in the upper layer and the lower layer has a swelling property when the tablet is in contact with an aqueous medium.

In order for an oral sustained-release tablet suitable for administration once daily to maintain the effective blood level even after 24 hours from the administration, a portion of the preparation in progress of gelation is needed to remain in the gastrointestinal tract as long as possible for at least 6 to 8 hours, preferably for at least 12 hours, after the administration.

In order to prepare a sustained-release tablet having the above property, particularly, the type and/or viscosity of the polymer should be considered.

As the swellable polymer comprised in the upper layer and the lower layer in the triple layer tablet of the present invention, polyethylene glycol, hypromellose, hydroxypropylcellulose, carboxymethylcellulose, polyvinyl alcohol, carbomer, etc. can be used.

The swellable polymer can be used alone or a mixture of two or more kinds of the polymers can be used. Or, two or more kinds of polymer mixtures, having properties suitable for the present invention, or copolymers can be properly used for the present invention.

In addition, the swellable polymer that can be used in the preparation of the present invention preferably shows a high viscosity. For example, the viscosity in 2% (w/w) aqueous solution (25° C.) is preferably 400 cps or more, and the viscosity in 1% (w/w) aqueous solution (25° C.) is more preferably 2,000 cps or more.

The upper layer and the lower layer may further comprise pharmaceutically acceptable excipients, for example, diluents or fillers. The amount of the excipients may be in the range of 50% (w/w) or less, preferably, in the range of 40% (w/w) or less, relative to the weight of each layer. The excipients can increase the physical property of the triple layer tablet while providing the fluidity of granule and hardness improvement of the tablet in the mixing and tableting process. Representative examples of the excipients include sugars (for example, dextrose, dextrate, dextrin, lactose, sucrose, glucose, mannitol, isomalt, xylitol, erythritol and sorbitol, etc.), cellulose (for example, crystalline cellulose, microcrystalline cellulose, microcrystalline cellulose silicide, low-substituted hydroxypropylcellulose, etc.), starch (for example, corn starch, potato starch, pre-gelatinized starch, etc.), salts (for example, sodium chloride, calcium carbonate, calcium hydrogen phosphate, calcium phosphate, magnesium carbonate, etc.), organic acids (for example, fumaric acids, tartaric acid, etc.) or a mixture thereof.

Meanwhile, even if the triple layer tablet of the present invention does not comprise binders, diluents or fillers in the upper layer and the lower layer, the swellable polymer of the upper layer and the lower layer can swell by a medium transfer agent of the intermediate layer.

The oral sustained-release triple layer tablet of the present can be prepared by a method comprising:

(i) a step of preparing a tableting blend for an upper layer and a lower layer consisting of a mixture in which pregabalin or a pharmaceutically acceptable salt thereof and a swellable polymer are mixed, or granules in which they are granulated;

(ii) a step of preparing a tableting blend for an intermediate layer consisting of a mixture in which pregabalin or a pharmaceutically acceptable salt thereof and a medium transfer agent are mixed, or granules in which they are granulated; and (iii) a step of preparing a triple layer tablet by tableting the blend prepared at the step (i) and the blend prepared at the step (ii).

In the preparation method, the tableting blend prepared at the step (i) may further comprise excipients, binders or lubricants, and the tableting blend prepared at the step (ii) may also further comprise binders or lubricants.

In addition, also at the step (iii), the tableting can be performed by further comprising lubricants.

The tableting blend prepared at the step (iii) is tableted according to typical methods. For example, the triple layer tablet of the present invention can be prepared by mixing the ingredient of each layer of the upper layer, intermediate layer and lower layer respectively using a mixer and then direct-tableting it using a multilayer tableting machine. Or, the triple layer tablet of the present invention can be prepared by mixing the ingredient of each layer to prepare a granule respectively using a high speed mixer, a fluidized-bed granulator or a roller compressor, etc. and adding a lubricant to make it lubricated, and then tableting it using a multilayer tableting machine.

The sustained-release preparation of the present invention can be prepared in a multilayer tablet consisting of three or more layers depending on cases.

EMBODIMENT OF THE INVENTION

Examples

Hereinafter, the present invention will be explained in more detail through the following examples. However, the following examples are only to exemplify the present invention, and the scope of the present invention is not limited to the following examples.

Examples 1 to 8

According to the component ratio (unit: mg) of the following table, pregabalin and polyethylene oxide (product name: Polyox WSR, Dow Chemicals) as a mixture to be used in the upper layer and the lower layer were mixed and passed through 25 mesh sieve. Thereafter, this mixture was mixed with magnesium stearate that passed through 30 mesh sieve.

In addition, pregabalin and the medium transfer agent as a mixture of the intermediate layer were mixed and passed through 25 mesh sieve. Thereafter, this mixture was mixed with magnesium stearate that passed through 30 mesh sieve.

The amount of each mixtures to be used in the upper layer, the lower layer and the intermediate layer was measured, and the oblong triple layer tablets (Examples 1 to 8) were prepared using a triple layer tableting machine or compressor.

TABLE 1

Compositions of Examples 1 to 4 (unit: mg)

| | | Example 1 | Example 2 | Example 3 | Example 4 |
|---|---|---|---|---|---|
| Upper layer | pregabalin | 45 | 120 | 60 | 60 |
| | polyethylene oxide (Polyox WSR 303) | 150 | 250 | 200 | 200 |
| | magnesium stearate | 3 | 5 | 4 | 4 |
| Intermediate layer | pregabalin | 60 | 60 | 30 | 30 |
| | lactose | 70 | | | |
| | dextrate | | 150 | | |
| | tartaric acid | | | 70 | |
| | microcrystalline cellulose | | | | 70 |
| | magnesium stearate | 2 | 3 | 1 | 1 |
| Lower layer | pregabalin | 45 | 120 | 60 | 60 |
| | polyethylene oxide (Polyox WSR 303) | 150 | 250 | 200 | 200 |
| | magnesium stearate | 3 | 5 | 4 | 4 |
| Total amount | | 528 | 963 | 629 | 629 |

TABLE 2

Compositions of Examples 5 to 8 (unit: mg)

| | | Example 5 | Example 6 | Example 7 | Example 8 |
|---|---|---|---|---|---|
| Upper layer | pregabalin | 60 | 75 | 60 | 60 |
| | polyethylene oxide (Polyox WSR 303) | 150 | 300 | | 150 |
| | polyethylene oxide (Polyox WSR N12K) | | | 200 | |
| | magnesium stearate | 3 | 5 | 4 | 2 |
| Intermediate layer | pregabalin | 30 | 10 | 30 | 30 |
| | dextrate | | 150 | | |
| | microcrystalline cellulose | | | 70 | |
| | hydroxypropyl methylcellulose | 20 | | | |
| | mannitol | 50 | 150 | | 45 |
| | tartaric acid | | | | 30 |
| | magnesium stearate | 1 | 5 | 1 | 1 |
| Lower layer | pregabalin | 60 | 75 | 60 | 60 |
| | polyethylene oxide (Polyox WSR 303) | 150 | 300 | | 150 |
| | polyethylene oxide (Polyox WSR N12K) | | | 200 | |
| | magnesium stearate | 3 | 5 | 4 | 2 |
| Total amount | | 527 | 1075 | 629 | 530 |

Test Example 1—Swelling Test

A tablet was put into a vessel containing 0.06N HCl 900 mL, and the mixture was stirred at a rotation speed of 50 rpm using USP dissolution method 2 (paddle). Then, the size of the tablet was measured using calipers over the time. The volume and volume increase rate of the tablet were calculated based on the following equation.

volume (mm$^3$)=major axis (mm)×minor axis (mm)× height (mm)

volume increase rate (%)=(volume at the measured time/volume at 0 hour (that is, just before the test))×100(%)

TABLE 3

| Time (hr) | | Example 1 | Example 2 | Example 3 | Example 4 | Example 5 | Example 6 | Example 7 | Example 8 |
|---|---|---|---|---|---|---|---|---|---|
| 0 | major axis (mm) | 14.0 | 19.9 | 18.1 | 18.0 | 15.0 | 19.9 | 18.0 | 16.1 |
| | minor axis (mm) | 8.0 | 8.8 | 8.1 | 8.0 | 8.5 | 8.8 | 8.0 | 8.1 |
| | Thickness (mm) | 6.1 | 7.0 | 5.8 | 5.8 | 5.6 | 7.4 | 5.7 | 5.3 |
| | Volume (mm$^3$) | 689.2 | 1229.4 | 844.2 | 833.7 | 712.4 | 1300.4 | 823.7 | 686.8 |
| | Volume increase rate (%) | 100.0 | 100.0 | 100.0 | 100.0 | 100.0 | 100.0 | 100.0 | 100.0 |
| 2 | major axis (mm) | 23.9 | 24.6 | 24.8 | 28.5 | 19.8 | 24.8 | 24.0 | 20.7 |
| | minor axis (mm) | 15.9 | 13.4 | 12.3 | 13.1 | 12.6 | 13.3 | 12.0 | 13.1 |
| | Thickness (mm) | 11.3 | 11.9 | 9.1 | 10.6 | 9.9 | 13.0 | 10.7 | 9.9 |
| | Volume (mm$^3$) | 4273.0 | 3922.5 | 2754.6 | 3959.4 | 2463.3 | 4283.4 | 3078.4 | 2678.1 |
| | Volume increase rate (%) | 620.0 | 319.1 | 326.3 | 474.9 | 345.8 | 329.4 | 373.7 | 389.9 |

TABLE 3-continued

| Time (hr) | | Example | | | | | | | |
|---|---|---|---|---|---|---|---|---|---|
| | | 1 | 2 | 3 | 4 | 5 | 6 | 7 | 8 |
| 6 | major axis (mm) | 28.6 | 28.4 | 28.8 | 33.5 | 22.3 | 30.3 | 27.5 | 24.8 |
| | minor axis (mm) | 18.1 | 14.3 | 14.3 | 16.4 | 12.5 | 14.5 | 13.4 | 16.7 |
| | Thickness (mm) | 10.4 | 11.9 | 13.0 | 12.4 | 10.1 | 14.9 | 11.8 | 11.3 |
| | Volume (mm$^3$) | 5349.1 | 4803.4 | 5348.2 | 6805.1 | 2814.6 | 6531.0 | 4350.8 | 4645.4 |
| | Volume increase rate (%) | 776.1 | 390.7 | 633.6 | 816.2 | 494.7 | 502.2 | 528.2 | 676.4 |

Figure 2:
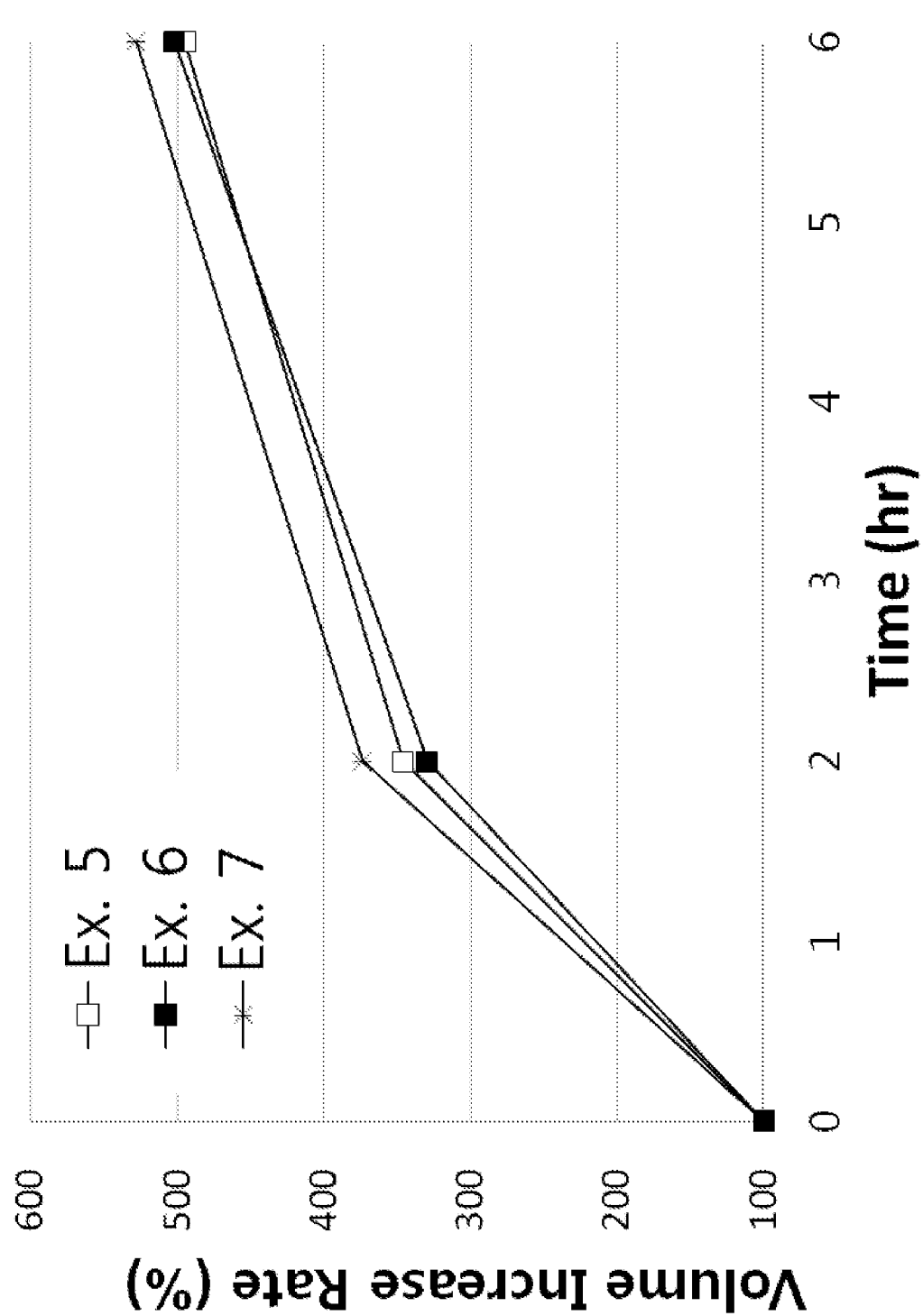
FIG. 2 is a graph comparing the volume changes in the swelling test of the pregabalin-containing oral sustained-release triple layer tablets prepared in Examples 5 to 7.

Referring to table 3, FIG. 1 and FIG. 2, it can be confirmed that in examples 1 to 8, the volume increase rate at 2 hours are rapidly increased to 300% or more, and the volume increase rate at 6 hours are increased more than the volume increase rate at 2 hours. In addition, it was confirmed that the major axis and the minor axis of the tablet can be maintained to 12 mn or more for 6 hours after swelling.

Test Example 2: Pharmacokinetic Test in Beagle Dogs

Pharmacokinetic test in beagle dogs was performed for the table of Example 8 as the test drug and the commercially available Lyrica capsule 75 mg as the control. About 11 kg of beagle dogs were divided into groups of 8 dogs. A capsule as the control drug was administrated twice at initial time and 10 hours later respectively. The tablet (test drug) of example 8 was administrated once daily. Blood was collected for 24 hours after the first administration, and then the blood was analyzed to calculate each pharmacokinetic parameter. The results are shown in the following table 4.

TABLE 4

| Parameter | Example 8 | Reference drug | percentage (example/reference drug) |
|---|---|---|---|
| AUC$_{24\ hr}$(μg · hr/mL) | 169.87 | 162.40 | 1.05 |
| C$_{max}$(μg/mL) | 13.34 | 15.75 | 0.85 |
| T$_{max}$(hr) | 5.9 | 10.7 (1$^{st}$peak: 0.9) | |

Figure 3:
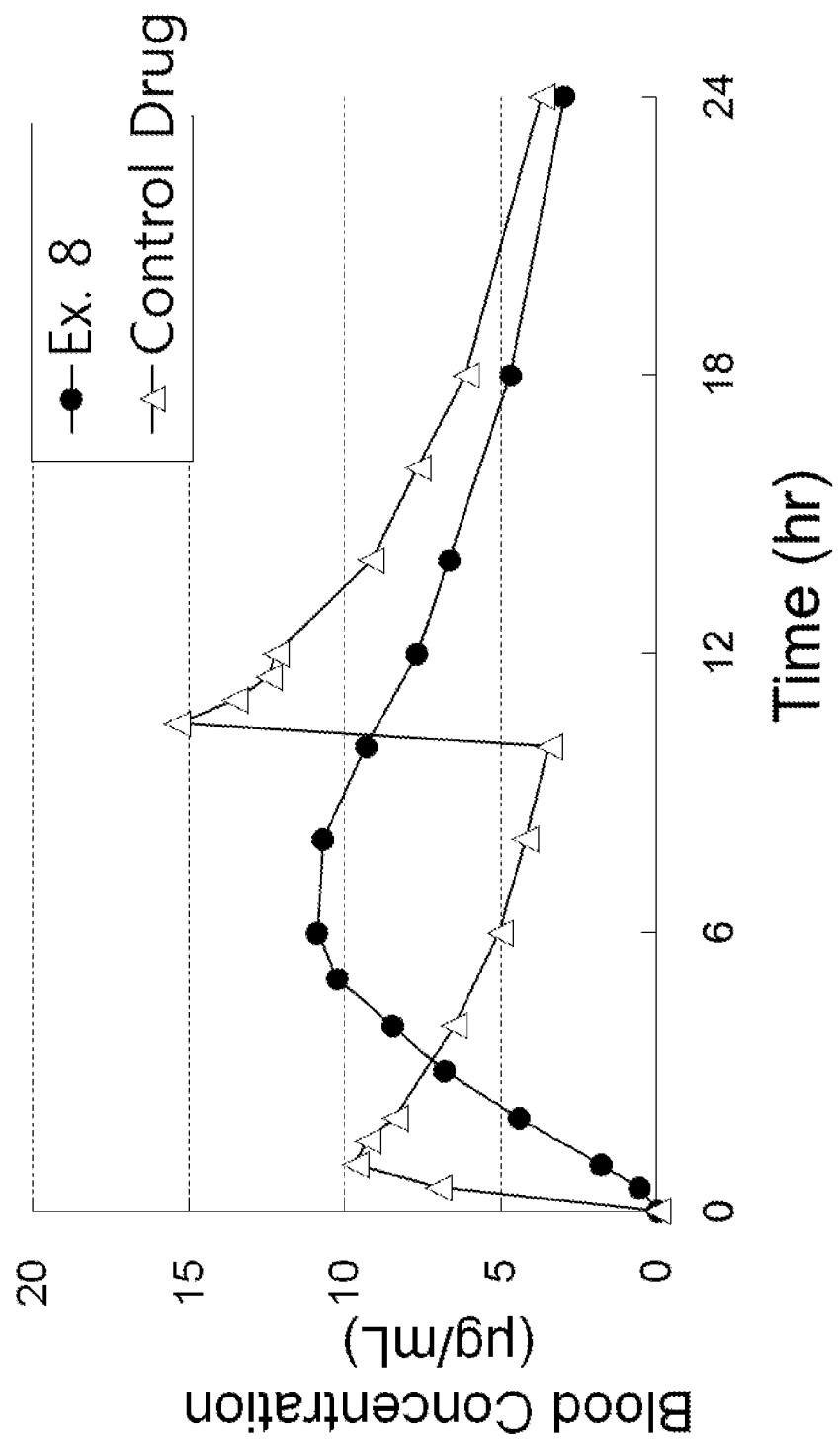
FIG. 3 is a graph showing the pharmacokinetic test results obtained by administering the tablet of Example 8 once and control agents (Lyrica® capsule) twice in beagle dogs, respectively.

As the test results of table 4 and FIG. 3, it was confirmed that example 8 in which the tablet was administered once daily has good absorption rate and extent as compared to the control drug that was administered twice daily. Accordingly, it can be understood that according to the preparation of the present invention, pregabalin can be administered once daily.

INDUSTRIAL APPLICABILITY

The preparation of the present invention comprising pregabalin can be administered once daily. Accordingly, the compliance can be greatly improved.

What is claimed is:

1. A multilayer tablet comprising:
   an upper layer and a lower layer comprising a swellable polymer; and
   an intermediate layer comprising a medium transfer agent, the intermediate layer being positioned between the upper layer and the lower layer,
   wherein the tablet comprises pregabalin or a pharmaceutically acceptable salt thereof as an active ingredient,
   wherein the upper layer, the lower layer, and the intermediate layer all comprise pregabalin or a pharmaceutically acceptable salt thereof, and
   wherein an amount of pregabalin in the intermediate layer is 40% or less of a total amount of pregabalin in the upper layer, the lower layer, and the intermediate layer.

2. The multilayer tablet according to claim 1, wherein the medium transfer agent absorbs the aqueous medium and transfers it to the upper layer and the lower layer.

3. The multilayer tablet according to claim 1, wherein the medium transfer agent is an excipient having solubility that 10 mL or less of water is required to dissolve the medium transfer agent of 1 g.

4. The multilayer tablet according to claim 1, wherein the medium transfer agent is hydrophilic.

5. The multilayer tablet according to claim 1, wherein the medium transfer agent is one or more selected from the group consisting of sugars, polyvinylpyrrolidone, salts, organic acids, starch, microcrystalline cellulose, and low-substituted hydroxypropylcelluloses.

6. The multilayer tablet according to claim 5, wherein the medium transfer agent is one or more selected from the group consisting of dextrose, dextrate, dextrin, lactose, sucrose, glucose, mannitol, isomalt, xylitol, erythritol, sorbitol, polyvinylpyrrolidone, sodium chloride, magnesium chloride, sodium phosphate, fumaric acids, tartaric acid, corn starch, potato starch, pre-gelatinized starch, microcrystalline cellulose, and low-substituted hydroxypropylcelluloses.

7. The multilayer tablet according to claim 1, wherein the swellable polymer is one or more selected from the group consisting of polyethylene oxide, hydroxypropyl methylcellulose, hydroxypropylcelluloses, carboxymethylcellulose, polyvinyl alcohol, and carbomer.

8. The multilayer tablet according to claim 1, wherein the tablet is orally administered once daily.

9. The multilayer tablet according to claim 1, wherein the amount of the medium transfer agent is 10 to 70% (w/w) relative to the total weight of the swellable polymer comprised in the upper layer and the lower layer of the multilayer tablet.

10. The multilayer tablet according to claim 1, wherein the upper layer and the lower layer further comprise pharmaceutically acceptable excipients, binders or lubricants.

11. The multilayer tablet according to claim 1, wherein the intermediate layer further comprises pharmaceutically acceptable binders or lubricants.

12. A method for preparing the multilayer tablet according to claim 1, comprising:
- (i) a step of preparing a tablet material for an upper layer and a lower layer comprising a mixture in which pregabalin or a pharmaceutically acceptable salt thereof and a swellable polymer are mixed, or a granulate in which they are granulated;
- (ii) a step of preparing a tablet mixture for an intermediate layer comprising a mixture in which pregabalin or a pharmaceutically acceptable salt thereof and a medium transfer agent are mixed, or a granulate in which they are granulated; and
- (iii) a step of preparing a triple layer tablet by tableting the tablet material prepared at the step (i) and the tablet material prepared at the step (ii).

* * * * *